July 22, 1952 H. A. M. VERSCHUREN Plant Pat. 1,115
ROSE PLANT
Filed July 11, 1951
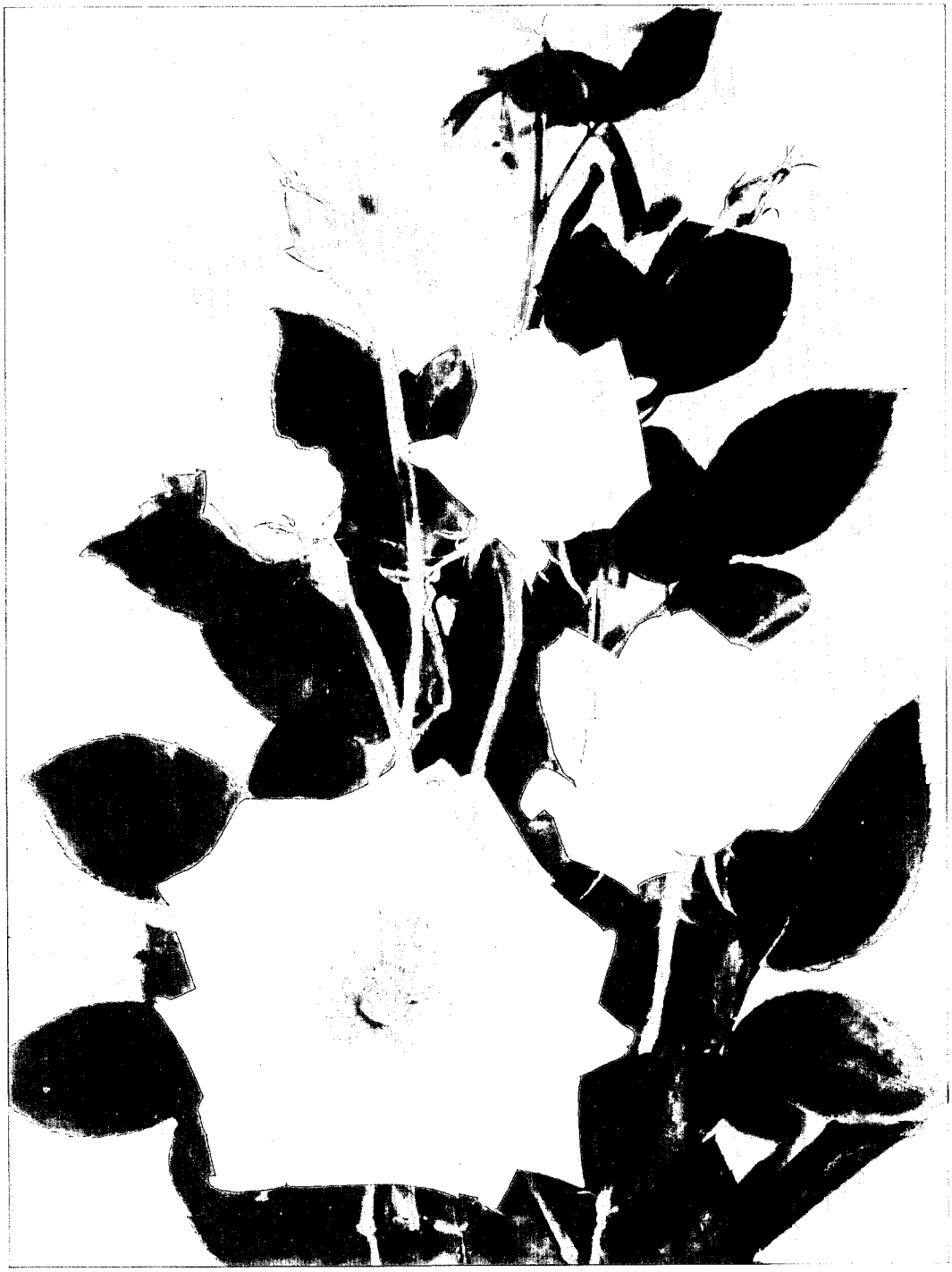
Inventor.
H. A. M. Verschuren
By: Robert Cobb
Attorneys.

Patented July 22, 1952

Plant Pat. 1,115

UNITED STATES PATENT OFFICE 1,115

ROSE PLANT

Hendrikus Antonie Maria Verschuren, Haps, Netherlands, assignor to Jackson & Perkins Company, Newark, N. Y., a corporation of New York Application July 11, 1951, Serial No. 236,104

1 Claim. (Cl. 47—61)

The present invention relates to a new and distinct variety of rose plant of the hybrid tea class, originated by me by crossing an unnamed seedling of "Kaiserin Auguste Victoria" (unpatented) with an unnamed and unpatented white seedling.

The primary objective in making this cross was to produce a vigorous white rose of better quality than the white roses heretofore available in commerce. This objective was fully achieved, as evidenced by the following unique and improved combination of characteristics which are outstanding and dominant in the new variety:

(1) The long stems on which the flowers are borne;

(2) The prolific growth of the plant;

(3) The general strength of the variety and its marked resistance to disease;

(4) The purer white color of the flowers;

(5) The unusual thickness of the flower petalage; and (6) The lasting quality of the flowers.

In comparison with its parent "Kaiserin Auguste Victoria," the new variety produces more and better flowers, and it is even better than the well-known and popular variety "White Briarcliff" (Plant Patent No. 108) due to the thicker petalage of its flowers and the more upright habit of growth of the plant.

Asexual reproduction of the new variety by budding at Newark, New York, and Pleasanton, California, shows that the foregoing characteristics and distinctions come true to form and are established and transmitted through succeeding propagations.

The accompanying drawing shows specimens of the flowers and foliage of the new variety in different stages of development.

The following is a detailed description of the new variety, with color terminology in accordance with Ridgway's Color Standards and Nomenclature:

Parentage: Seedling.

*Seed parent.*—"Kaiserin Auguste Victoria."

*Pollen parent.*—An unnamed white seedling.

Classification: Botanic and commercial—hybrid tea.

*Flower*

(Observations made at Newark, New York, in the greenhouse in the morning, early in the month of April.)

Blooming habit: Recurrent—continuous.

Bud:

*Size.*—Large.

*Form.*—Ovoid. Is not affected by wet or hot weather.

*Color.*—When sepals first divide—Light Dull Green-Yellow, Plate 17. When petals begin to unfurl—Pale Dull Green-Yellow, Plate 17. When half blown—inside of petals: White, Plate 53, overcast with Sea-Foam Yellow, Plate 31, at the lower half of the petal; reverse of petals: White, Plate 53, overcast with Sea-Foam Green, Plate 31, at the lower half of the petal.

*Sepals.*—Branched; "hood" above bud. Curl back when petals begin to unfurl. Color—inside: Kildare Green, Plate 31; outside: Lettuce Green, Plate 5.

*Calyx.*—Shape — funnel. Size — long. Aspect—Smooth. Odor when rubbed—none. Color—Oil Green, Plate 5.

*Peduncle.*—Length — medium. Aspect—smooth. Color—Parrot Green, Plate 6. Strength—erect; heavy.

*Opening.*—Opens up well. Is not affected by adverse weather conditions.

Bloom:

*Size.*—Large. Average size when fully expanded—4½ inches to five inches.

*Borne.*—Singly and several together.

*Stem.*—Long; strong.

*Form.*—When first open—high center. Permanence—retains its form to the end.

*Petalage.*—Double (full but open center). Number of petals under normal conditions—30.

(Description made from a freshly opened bloom cut early in the morning and taken indoors or in shade.)

*Color.*—Center of flower—White, Plate 53, slightly overcast with Sulphur Yellow, Plate 5, at the lower half of the petal. Outer petals—White, Plate 53. Base of petals (aiglet)—Pale Greenish Yellow, Plate 5. Inside of petals—White, Plate 53. Reverse of petals—White, Plate 53. General tonality from a distance—White, Plate 53.

*Discoloration.*—General tonality at end of first day—White, Plate 53. Second day—White, Plate 53. Third day—White, Plate 53.

Petals:

*Texture.*—Thick. Is not affected by wet or hot weather.

*Appearance.*—Inside — shiny; outside—satiny.

*Form.*—Round.

*Arrangement.*—Imbricated (regularly arranged shingle-like). Petaloids in center—few; small.

*Persistence.*—Drop off cleanly.

*Fragrance.*—Moderate. Nature—tea (average hybrid tea scent).

*Lasting quality.*—On the plant and as cut flower—long.

*Genital organs*

Stamens, anthers: Large; many. Color—Light Cadmium Yellow, Plate 4. Arrangement—regular around styles.

Stamens, filaments (threads): Long. Color—Nopal Red, Plate 1.

Pollen: Color—Buff Yellow, Plate 4.

Styles: Bunched; uneven length; medium length; thin.

Stigmas: Color—Picric Yellow, Plate 4.

Ovaries: Some protruding from calyx.

*Plant*

Form: Bush.

Growth: Vigorous; upright.

Foliage: 5 to 7 leaflets.

*Size.*—Large.

*Quantity.*—Normal.

*Color.*—New foliage—upper side: Yellowish Oil Green, Plate 5; under side: Yellowish Oil Green, Plate 5, overcast with Garnet Brown, Plate 1. Old Foliage—upper side: Forest Green, Plate 17; serrations Oxblood Red, Plate 1; under side: Light Hellebore Green, Plate 17.

*Shape.*—Oval pointed.

*Texture.* — Upper side — glossy; smooth. Under side—smooth. Ribs and veins—prominent.

*Edge.*—Serrated (saw toothed).

*Serration.*—Double; small.

*Leaf stem.*—Color—Hay's Russet, Plate 14. Under side—prickles.

*Stipules.*—Medium length; bearded.

*Disease resistance.*—Resistant.

Wood:

*New wood.*—Color—Hay's Russet, Plate 14. Bark—smooth.

*Old wood.*—Color—Yellowish Oil Green, Plate 5. Bark—smooth.

Thorns:

*Quantity.*—On main stalks from base and on laterals from stalk—ordinary.

*Form.*—Narrow base; medium length; slightly hooked downward.

*Color when young.*—Old Rose, Plate 13.

*Position.*—Irregular.

Prickles: On main stalks and on laterals—none.

Short Needles: On main stalks and on laterals—none.

I claim:

A new and distinct variety of rose plant of the hybrid tea class, characterized as to novelty by its prolific and upright growth, general strength and resistance to disease, by the abundance and pure white color of its flowers and the long stems on which they are borne, by the thickness of the flower petalage, and by the lasting quality of the flowers, substantially as herein shown and described.

HENDRIKUS ANTONIE MARIA VERSCHUREN.

No references cited.